US009556109B1

(12) United States Patent
Caran et al.

(10) Patent No.: US 9,556,109 B1
(45) Date of Patent: Jan. 31, 2017

(54) TRISCATIONIC AMPHIPHILE DERIVATIVE COMPOUNDS HAVING A PENDENT ALCOHOL GROUP, COMPOSITIONS THEREOF, AND METHODS FOR MAKING SAME

(71) Applicant: James Madison Innovations, Inc., Harrisonburg, VA (US)

(72) Inventors: Kevin L. Caran, Staunton, VA (US); Kyle Seifert, Harrisonburg, VA (US)

(73) Assignee: JAMES MADISON INNOVATIONS, INC., Harrisonburg, VA (US)

( * ) Notice: Subject to any disclaimer, the term of this patent is extended or adjusted under 35 U.S.C. 154(b) by 0 days.

(21) Appl. No.: 15/225,522

(22) Filed: Aug. 1, 2016

Related U.S. Application Data

(60) Provisional application No. 62/199,937, filed on Jul. 31, 2015.

(51) Int. Cl.
*C07C 215/14* (2006.01)
*A01N 33/12* (2006.01)

(52) U.S. Cl.
CPC ............. *C07C 215/14* (2013.01); *A01N 33/12* (2013.01)

(58) Field of Classification Search
CPC .............................. A01N 33/12; C07C 215/14
USPC ......................................................... 514/643
See application file for complete search history.

(56) References Cited

PUBLICATIONS

Mosbach et al. Anal. Chem. 2001, 73 ,2468-2475.*
Janka Karlovsk, Andre A. Williams, Richard V. Macri, Richard D. Gandour, Sergio S. Funari, Daniela Uhrikova, Pavol Balgav; Synchrotron SAX and WAX diffraction study of a hydrated very long-chain, dendritic amphiphile + DPPC mixture. Colloids and Surfaces B: Biointerfaces 54 (2007) 160-164.
Eko W. Sugandhia, Carla Slebodnicka, Joseph O. Falkinham III, Richard D. Gandour; Synthesis and antimicrobial evaluation of water-soluble, dendritic derivatives of epimeric 5α-cholestan-3-amines and 5α-cholestan-3-yl aminoethanoates. Steroids 72 (2007) 615-626.
Sugandhi, E. W.; Falkinham III, J. O.; Gandour, R. D. Synthesis and antimicrobial activity of symmetrical two-tailed dendritic tricarboxylato amphiphiles. Bioorg. Med. Chem. 2007, 15, 3842-3853.
Williams, A. A.; Sugandhi, E. W.; Macri, R. V.; Falkinham, J. O.; Gandour, R. D. Antimicrobial activity of long-chain, water-soluble, dendritic tricarboxylato amphiphiles. Journal of Antimicrobial Chemotherapy. 2007, 59, 451-458.
Karolina Z. Roszak, Stephanie L. Torcivia, Kristina M. Hamill, Addie R. Hill, Kristen R. Radloff, David M. Crizer, Angela M. Middleton, Kevin L. Caran; Biscationic bicephalic (double-headed) amphiphiles with an aromatic spacer and a single hydrophobic tail. Journal of Colloid and Interface Science 331 (2009) 560-564.

Macri, R. V.; Karlovská, J.; Doncel, G. F.; Du, X.; Maisuria, B. B.; Williams, A. A.; Sugandhi, E. W.; Falkinham III, J. O.; Esker, A. R.; Gandour, R. D. Comparing anti-HIV, antibacterial, antifungal, micellar, and cytotoxic properties of tricarboxylato dendritic amphiphiles. Bioorg. Med. Chem. 2009, 17, 3162-3168.
Maisuria, B. B.; Actis, M. L.; Hardrict, S. N.; Falkinham III, J. O.; Cole, M. F.; Cihlar, R. L.; Peters, S. M.; Macri, R. V.; Sugandhi, E. W.; Williams, A. A.; Poppe, M. A.; Esker, A. R.; Gandour, R. D. Comparing micellar, hemolytic, and antibacterial properties of di- and tricarboxyl dendritic amphiphiles. Bioorg. Med. Chem. 2011, 19, 2918-2926.
Falkinham III, J. O.; Macri, R. V.; Maisuria, B. B.; Actis, M. L.; Sugandhi, E. W.; Williams, A. A.; Snyder, A. V.; Jackson, F. R.; Poppe, M. A.; Chen, L.; Ganesh, K.; Gandour, R. D. Antibacterial activities of dendritic amphiphiles against nontuberculous mycobacteria. Tuberculosis. 2012, 92, 173-181.
Riya J. Muckom, Francesca Stanzione, Richard D. Gandour, Amadeu K. Sum; Dendritic Amphiphiles Strongly Affect the Biophysical Properties of DPPC Bilayer Membranes. J. Phys. Chem. B 2013, 117, 1810-1818.
Black, J. W.; Jennings, M. C.; Azarewicz, J.; Paniak, T. J.; Grenier, M. C.; Wuest, W. M.; Minbiole, K. P. C. TMEDA-derived biscationic amphiphiles: An economical preparation of potent antibacterial agents. Bioorg. Med. Chem. Lett. 2014, 24, 99-102.
Megan C. Jennings, Laura E. Ator, Thomas J. Paniak, Kevin P. C. Minbiole, William M. Wuest; Biofilm-Eradicating Properties of Quaternary Ammonium Amphiphiles: Simple Mimics of Antimicrobial Peptides. ChemBioChem 2014, 15, 2211-2215.
Thomas J. Paniak, Megan C. Jennings, Paul C. Shanahan, Maureen D. Joyce, Celina N. Santiago, William M. Wuest, Kevin P. C. Minbiole; The antimicrobial activity of mono-, bis-, his-, and tetracationic amphiphiles derived from simple polyamine platforms. Bioorganic & Medicinal Chemistry Letters 24 (2014) 5824-5828.
John N. Marafino, Tara M. Gallagher, Jhosdyn Barragan, Brandi L. Volkers, Jade E. LaDow, Kyle Bonifer, Gabriel Fitzgerald, Jason L. Floyd, Kristin McKenna, Nicholas T. Minahan, Brenna Walsh, Kyle Seifert, Kevin L. Caran; Colloidal and antibacterial properties of novel triple-headed, double-tailed amphiphiles: Exploring structure-activity relationships and synergistic mixtures. Bioorganic & Medicinal Chemistry 23 (2015) 3566-3573.
Megan C. Jennings, Kevin P. C. Minbiole, William M. Wuest; Quaternary Ammonium Compounds: An Antimicrobial Mainstay and Platform for Innovation to Address Bacterial Resistance. ACS Infect. Dis. 2015, 1, 288-303.

(Continued)

*Primary Examiner* — Yevegeny Valenrod
(74) *Attorney, Agent, or Firm* — David Grossman; Lee Heiman

(57) ABSTRACT

The inventive subject matter relates to compounds of Formula I, compositions thereof, and processes for making such compounds as further described herein. The inventive compounds and compositions have antimicrobial properties and are useful as environmental disinfectants, topical cleansers such as topical personal care compositions, sanitizers, preservatives, in water treatment, as permanent or erodible coatings for medical devices and appliances, and in therapeutics. Additionally, the compounds of Formula I will serve as synthetic intermediates for making additional novel derivatives of triscationic amphiphile compounds.

20 Claims, 2 Drawing Sheets

(56) References Cited

PUBLICATIONS

Megan C. Jennings, Bettina A. Buttaro, Kevin P. C. Minbiole, William M. Wuest; Bioorganic Investigation of Multicationic Antimicrobials to Combat QAC-Resistant *Staphylococcus aureus*. ACS Infect. Dis. 2015, 1, 304-309.

Haldar, J.; Kondaiah, P.; Bhattacharya, S. Synthesis and antibacterial properties of novel hydrolyzable cationic amphiphiles. Incorporation of multiple head groups leads to impressive antibacterial activity. J. Med. Chem. 2005, 48, 3823-3831.

Sugandhi, E. W.; Macri, R. V.; Williams, A. A.; Kite, B. L.; Slebodnick, C.; Falkinham, J. O.; Esker, A. R.; Gandour, R. D. Synthesis, Critical Micelle Concentrations, and Antimycobacterial Properties of Homologous, Dendritic Amphiphiles. Probing Intrinsic Activity and the "Cutoff" Effect. J. Med. Chem. 2007, 50, 1645-1650.

Ladow, J. E.; Warnock, D. C.; Hamill, K. M.; Simmons, K. L.; Davis, R. W.; Schwantes, C. R.; Flaherty, D. C.; Willcox, J. A. L.; Wilson-Henjum, K.; Caran, K. L.; Minbiole, K. P. C.; Seifert, K. Bicephalic amphiphile architecture affects antibacterial activity. Eur. J. Med. Chem. 2011, 46, 4219-4226.

Grenier, M. C.; Davis, R. W.; Wilson-Henjum, K. L.; LaDow, J. E.; Black, J. W.; Caran, K. L.; Seifert, K.; Minbiole, K. P. C. The antibacterial activity of 4,4'-bipyridinium amphiphiles with conventional, bicephalic and gemini architectures. Bioorg. Med. Chem. Lett. 2012, 22, 4055-4058.

Ator, L. E.; Jennings, M. C.; McGettigan, A. R.; Paul, J. J.; Wuest, W. M.; Minbiole, K. P. C. Beyond paraquats: dialkyl 3,3'- and 3,4'-bipyridinium amphiphiles as antibacterial agents. Bioorg. Med. Chem. Lett. 2014, 24, 3706-3709.

* cited by examiner

1, R=C$_8$H$_{17}$ (*M-E,8,8*)
2, R=C$_{10}$H$_{21}$ (*M-E,10,10*)
3, R=C$_{12}$H$_{25}$ (*M-E,12,12*)
4, R=C$_{14}$H$_{29}$ (*M-E,14,14*)
5, R=C$_{16}$H$_{33}$ (*M-E,16,16*)

TRISCATIONIC AMPHIPHILE DERIVATIVE COMPOUNDS HAVING A PENDENT ALCOHOL GROUP, COMPOSITIONS THEREOF, AND METHODS FOR MAKING SAME

CROSS-REFERENCE TO RELATED APPLICATIONS

This application claims benefit of U.S. Provisional Application No. 62/199,937, filed Jul. 31, 2015, the contents of which is hereby incorporated by reference.

STATEMENT REGARDING FEDERALLY SPONSORED RESEARCH

This application relates in part to work performed under National Science Foundation Research Experiences for Undergraduates Grant No. CHE-1461175. As a result of this support, the government has rights in the invention.

BACKGROUND OF THE INVENTIVE SUBJECT MATTER

Field of Inventive Subject Matter

The inventive subject matter relates to compounds of Formula I, compositions thereof, and processes for making such compounds as further described herein. The inventive compounds and compositions have antimicrobial properties and are useful as environmental disinfectants, topical cleansers such as topical personal care compositions, sanitizers, preservatives, in water treatment, as permanent or erodible coatings for medical devices and appliances, and in therapeutics. Additionally, the compounds of Formula I will serve as synthetic intermediates for making additional novel derivatives of triscationic amphiphile compounds, such as dimers of compounds of Formula I, other polymers of compounds of Formula I, and dimers and other polymers of compounds of Formula I dimerized or polymerized with other triscationic amphiphile compounds.

Background

Over the last few decades, the overuse of antibiotics and antimicrobial compositions has decreased their effectiveness, contributing to bacterial acquired resistance. In addition, the production of novel antimicrobials continues to decrease due to low financial return. This decline in the development of novel antimicrobials, combined with the misusage and over prescription of antibiotics, has contributed to the increasing prevalence of antimicrobial-resistant infections (ARIs), especially in the hospital setting. ARIs have contributed to more than 25,000 deaths in member states of the European Union, Iceland, and Norway and 23,000 deaths in the United States. Hospitals and nursing homes are particularly prone to harboring antimicrobial-resistant organisms due to the frequent use of antimicrobial agents and influx of infected patients.

Limiting the transmission of bacteria between individuals and contaminated equipment is critical to reducing or preventing hospital-acquired infections and reducing mortality rates for patients and those that come into contact with them. Further, the development of biofilm contaminations on hospital surfaces such as urinary catheters, central venous catheters, and dental syringes is also a growing concern.

The development of effective novel disinfectants, antimicrobial coatings, topical treatments for infections, and antimicrobial drugs are all highly desirable solutions to these problems and are expected to reduce the transmission of pathogens, decrease the risk of infection by antibiotic resistant organisms, and provide new therapeutic treatments.

The antimicrobial activity of cationic amphiphiles—compounds with hydrophobic and positively charged hydrophilic regions—was first reported in 1935 Amphiphiles continue to be utilized as antimicrobial agents in detergents, disinfectants, cosmetics, and other common household products. A large variety of novel amphiphiles has been synthesized in an effort to increase antimicrobial effectiveness and specificity.

SUMMARY OF THE INVENTIVE SUBJECT MATTER

Applicants have developed a new class of compounds which exhibit effective antimicrobial properties and will overcome current bacterial resistance.

For the inventive compounds, the log of critical aggregation concentration and heat of aggregation for tested compounds were both inversely proportional to the length of the linear hydrocarbon chains. Antibacterial activity was optimal at a tail length of 12 carbons per chain, above which activity decreased. Among the compounds tested, the derivatives with two 12 carbon chains had the best antibacterial activity, killing all tested strains at concentrations of 2-4 µM for Gram-positive and 4-8 µM for Gram-negative bacteria. In the examples it has been shown, and it is expected for other compounds within the described class, that the antibacterial activity of several binary combinations of amphiphiles from this study will be higher than activity of individual amphiphiles, and that these combinations are synergistic. These amphiphiles are novel antibacterial agents that can be used in a variety of applications.

Thus, the inventive subject matter relates to compounds of Formula I, compositions thereof, and processes for making such compounds as further described herein.

FORMULA I

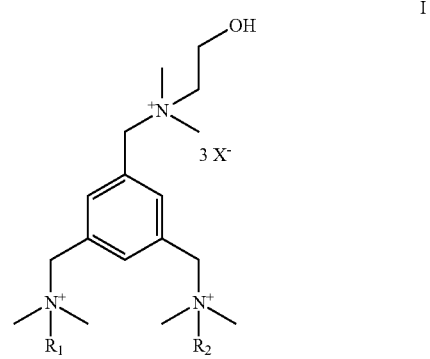

A compound of Formula I or a biologically acceptable salt, ester, or solvate thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;

m equals 1 to about 22; and n equals 1 to about 22.

The inventive compounds and compositions have antimicrobial properties and are useful as environmental disinfectants, topical cleansers, sanitizers, preservatives, in water treatment, as permanent or erodible coatings for medical devices and appliances, and in topical and/or systemic therapeutic formulations.

DETAILED DESCRIPTION OF EMBODIMENTS

Definitions

Figure 1:
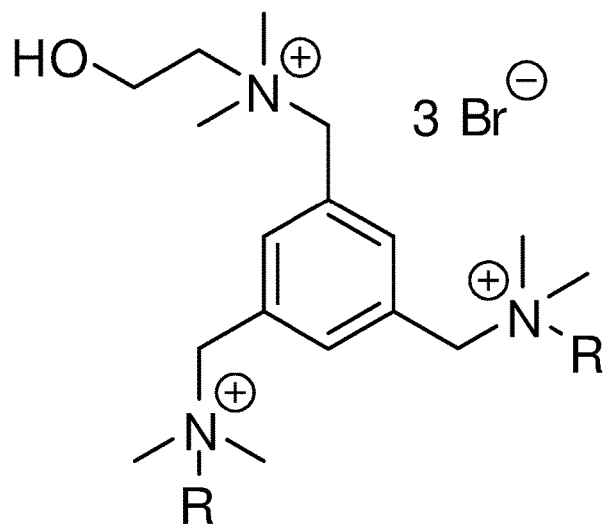
FIG. 1 is a drawing which depicts the basic structures of the inventive triple-headed, double-tailed amphiphile compounds having a pendent alcohol group, and showing the R groups for compounds 1-5.
Figure 2:
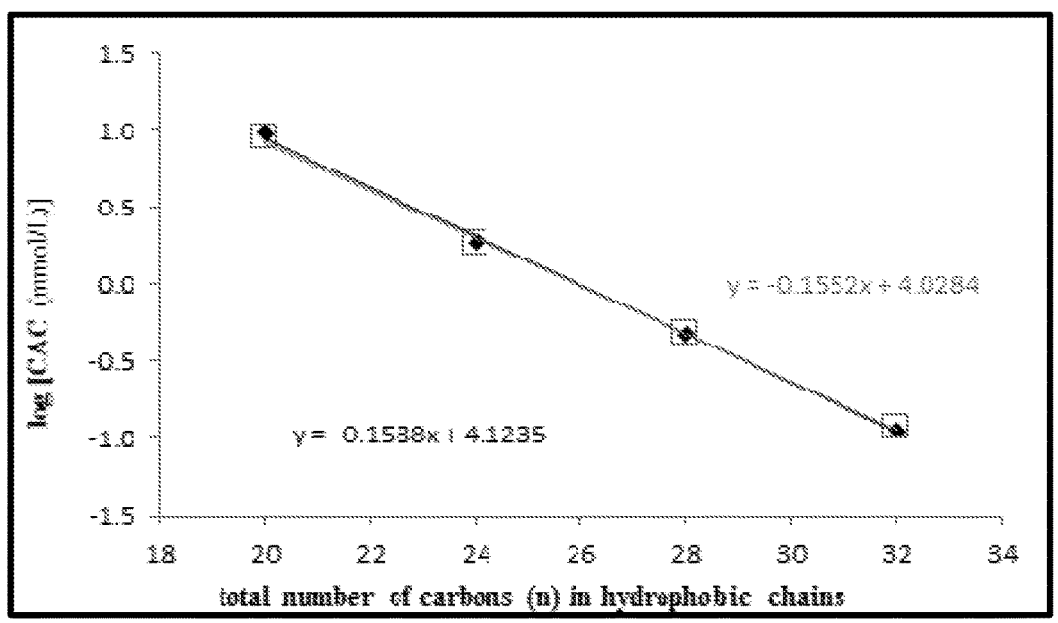
FIG. 2 is a graph which depicts a plot of log(CAC) versus tail length for tested compounds.

The terms "amphiphile" and "amphiphile compound" as used herein refer to compounds of Formula I, which may also be referred to herein more specifically as amphiphile compounds having a pendent alcohol group. These terms are used interchangeably throughout this disclosure.

The term "pharmaceutically acceptable salt, ester, or solvate" refers to a salt, ester, or solvate of a subject compound which possesses the desired pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Water or oil-soluble or dispersible products are thereby obtained.

It is to be understood that, in its most common form, a "reactant compound" or "intermediate" within the scope of the inventive subject matter may or may not have the reactive moiety(ies) necessary to produce a compound of the inventive subject matter. It is intended that such compound(s) optionally may be derivatized to add one or more reactive moiety(ies) by means known to one of ordinary skill in the art. By way of example and not limitation, appropriate derivatives may be produced by hydration, halogenation, carboxylation, amination, nitration, and sulfonation.

The term "reaction product" refers to that part of a reactant compound remaining after the chemical reaction producing a covalently-linked compound of the inventive subject matter, either an intermediate of final compound. Such chemical reactions include substitution, elimination, addition, oxidation, and reduction reactions, and involve reactive moieties such as multiple bonds; oxygen and hydroxyl; nitrogen, nitro, amide, and amine; sulfur, sulfhydryl, and sulpho; and other common groups known to one of ordinary skill in the art.

Subject Matter

The inventive subject matter relates to novel triscationic amphiphile compounds and compositions of Formula I, as well as processes for making compounds of Formula I. Also within the scope of the inventive subject matter are methods of inhibiting bacterial growth comprising contacting a bacteria with any of the inventive compounds described herein.

Amphiphile structure, including size and relative number of hydrophobic tails and hydrophilic head groups, governs colloidal characteristics including the critical aggregation concentration (CAC) and thermodynamic properties. At concentrations below the CAC, amphiphiles tend to align at the air-water interface in equilibrium with dissolved monomers in solution. At concentrations above the CAC, amphiphiles form aggregates in which hydrocarbon tails interact with each other, releasing water that was formerly associated with the tails, resulting in a second equilibrium between monomers and aggregates in solution. An increase in entropy typically associated with aggregate formation is generally attributed in large part to the release of water molecules surrounding hydrophobic units to the bulk water that accompanies this process. Increasing amphiphile hydrophobicity (for example by increasing the length or number of tails) decreases water solubility, thus decreasing CAC. In contrast, additional head groups can increase amphiphile solubility, typically resulting in a higher CAC.

Applicants have determined that amphiphile structure also affects antimicrobial activity and effectiveness. There is often a direct relationship between amphiphile tail length and the minimum inhibitory concentration (MIC), the lowest concentration at which an antimicrobial is able to inhibit bacterial growth. Typically, as tail length increases the MIC decreases until an optimal tail length is reached, while antibacterial activity then begins to decrease for amphiphiles with tail lengths exceeding the optimal length.

The number, type and variations in spacing between head group(s) also affects antibacterial activity. However, Applicants have determined that the relationship between head group structure and function is not as straightforward. Increasing the number of head groups can increase or decrease the MIC depending on the structure of the head group and counterion. Different amphiphile core structures and variations in spacing between head groups can also impact the MIC. When comparing spacing between head groups, amphiphiles with a 5-carbon spacer between two cationic head groups were found to be the most biologically active.

Applicants have also determined that some mixtures of two or more amphiphiles may exhibit synergy—the inhibition of bacteria at lower concentrations than when each amphiphile is used separately. By decreasing the required concentration of compounds, combination therapy reduces the potential for, or degree of, adverse side effects and increases the effectiveness of antibacterial agents. The improved efficacy of synergistic combinations has contributed to the improvement of hand disinfectants and effective treatment for patients with ARIs.

The inventive subject matter comprises the synthesis, as well as the colloidal, antibacterial, and synergistic characteristics, for two novel series of triple headed, double tailed amphiphiles, referred to herein as the M-E series and depicted in FIG. 1. Compounds are named as follows: M-E,n,n where M refers to the Mesitylene core, and n represents the number of carbon atoms in the alkyl group of a dimethylalkylammonium, e.g., 1=trimethylammonium; 8=octyldimethylammonium.

Exemplary amphiphiles in this application consist of three cationic head groups connected to a mesitylene core. Two of the head groups are trimethylammoniums that further connect to hydrocarbon tails varying in length found 1 to 22 carbons, preferably from 8 to 16 carbons. Although both series of amphiphiles are similar in structure to conventional Gemini amphiphiles, they are novel due to a trimethylammonium head group having a pendent alcohol group for the M-E series.

Although there may be no direct relationship between an amphiphile's colloidal and antimicrobial properties, both are clearly and profoundly affected by amphiphile structure. Developing a deeper understanding of these structure-function relationships provides insight into the mechanism by which amphiphiles interact with and inhibit bacterial growth. These particular architectures are expected to be highly effective disinfectants, likely through a mechanism that disrupts the bacterial membrane. The three cationic head groups are expected to interact with the net negative bacterial membrane, allowing the intercalation of the amphiphile's hydrophobic tails. This, in essence, appears to anchor the amphiphile in the membrane, creating disruption via the rigid mesitylene core and three cationic head groups.

To address this need, Applicants have developed a novel series of amphiphiles, which were synthesized and for which structure-activity relationships were investigated. Log (CAC) decreased linearly with increasing tail length for both series. For most of the amphiphiles tested, the MIC is significantly below the CAC, indicating amphiphile aggregation is not necessary for antibacterial activity. MIC values also indicated an optimal tail length of 12 carbons for each series as compound 3 (M-E,12,12) had the lowest MIC against all strains tested. These amphiphiles will prove useful in the medical field as surface disinfectants, antiseptics, or in topical treatments for treating or preventing infection with antibiotic-resistant organisms.

Inventive Compounds

Thus, the inventive subject matter relates to compounds of formulas I:

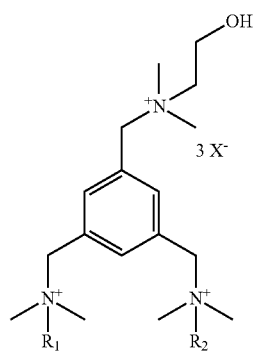

or a biologically acceptable salt, ester, or solvate thereof, wherein:

$R_1$ is independently selected from the group consisting of straight or branched chain $C_n$ alkyl, alkenyl, or alkynyl;
$R_2$ is independently selected from the group consisting of straight or branched chain $C_m$ alkyl, alkenyl, or alkynyl;
X is a counterion selected from the group consisting of $CO_3^{(2-)}$, $SO_4^{(2-)}$, $S_2O_3^{(2-)}$, $H_2PO_4^{(-)}$, $NO_3^{(2-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;
m equals 1 to about 22; and
n equals 1 to about 22.

In a preferred embodiment, $R_1$ is independently selected from the group consisting of straight or branched chain $C_n$ alkyl; and $R_2$ is independently selected from the group consisting of straight or branched chain $C_m$ alkyl.

In a more preferred embodiment, $R_1$ is independently selected from the group consisting of straight chain $C_{2-18}$ alkyl; and $R_2$ is independently selected from the group consisting of straight chain $C_{2-18}$ alkyl.

In a more preferred embodiment, $R_1$ is independently selected from the group consisting of straight chain $C_{8-16}$ alkyl; and $R_2$ is independently selected from the group consisting of straight chain $C_{8-16}$ alkyl.

In a more preferred embodiment, $R_1$ is independently selected from the group consisting of straight chain $C_{10-14}$ alkyl; and $R_2$ is independently selected from the group consisting of straight chain $C_{10-14}$ alkyl.

In a more preferred embodiment, $R_1$ is $C_{12}$ alkyl; and $R_2$ is $C_{12}$ alkyl.

In another preferred embodiment, X is halogen.

In more preferred embodiment, X is bromine.

Inventive Antimicrobial Methods

The inventive subject matter also relates to a method for inhibiting bacterial growth, comprising contacting a bacteria with a composition comprising (i) a compound of Formula I or (ii) a combination of two or more compounds, each independently selected from the group consisting of a compound of Formula I

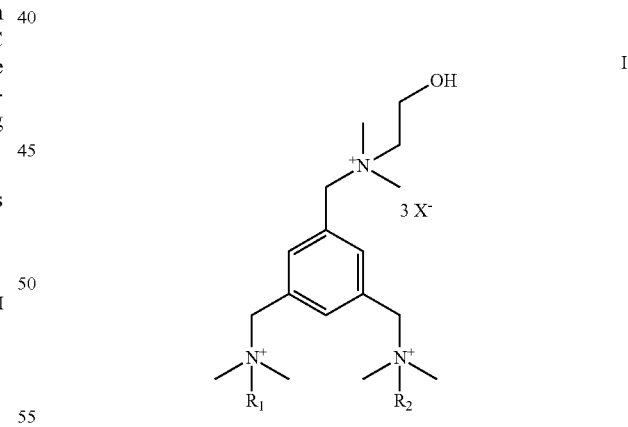

or a biologically acceptable salt, ester, or solvate thereof, wherein:

$R_1$ is independently selected from the group consisting of straight or branched chain $C_n$ alkyl, alkenyl, or alkynyl;
$R_2$ is independently selected from the group consisting of straight or branched chain $C_m$ alkyl, alkenyl, or alkynyl;
X is a counterion selected from the group consisting of $CO_3^{(2-)}$, $SO_4^{(2-)}$), $S_2O_3^{(2-)}$, $H_2PO_4^{(-)}$, $NO_3^{(2-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;

m equals 1 to about 22; and n equals 1 to about 22.

In a preferred embodiment, $R_1$ is independently selected from the group consisting of straight or branched chain $C_n$ alkyl; and $R_2$ is independently selected from the group consisting of straight or branched chain $C_m$ alkyl.

In a more preferred embodiment, $R_1$ is independently selected from the group consisting of straight chain $C_{2-18}$ alkyl; and $R_2$ is independently selected from the group consisting of straight chain $C_{2-18}$ alkyl.

In a more preferred embodiment, $R_1$ is independently selected from the group consisting of straight chain $C_{8-16}$ alkyl; and $R_2$ is independently selected from the group consisting of straight chain $C_{8-16}$ alkyl.

In a more preferred embodiment, $R_1$ is independently selected from the group consisting of straight chain $C_{10-14}$ alkyl; and $R_2$ is independently selected from the group consisting of straight chain $C_{10-14}$ alkyl.

In a more preferred embodiment, $R_1$ is $C_{12}$ alkyl; and $R_2$ is $C_{12}$ alkyl.

In another preferred embodiment, X is halogen.

In more preferred embodiment, X is bromine.

Antimicrobial Uses

As contemplated at the time of filing this application, Applicants expect that the antimicrobial properties of the inventive compounds and compositions will find a primary use as environmental disinfectants and sanitizers, addressing the needs described above for limiting the transmission of bacteria between individuals and contaminated equipment, as well as the increasing prevalence of antimicrobial-resistant infections, in critical health care settings such as hospitals and nursing homes. Thus, within the scope of the inventive subject matter are methods of inhibiting bacterial growth comprising contacting a bacteria with any of the inventive compounds or compositions, or combinations thereof, described herein.

Additional uses for the inventive compounds and compositions include topical personal care compositions; as permanent or erodible coatings for medical devices and appliances; preservatives; in water treatment; and as therapeutics, whether topical or systemic.

Exemplary but non-limiting topical uses may include deodorants, antiperspirants, antiperspirant/deodorants, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, nonwoven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, and drug delivery systems for topical application of medicinal compositions that are to be applied to the skin.

Exemplary but non-limiting uses as coatings, whether permanent or erodible, for articles of manufacture such as medical devices and appliances, include coatings for medical equipment, appliances, and devices; medical supplies such as catheters, sutures and staples, syringes and needles, implants, prosthetics, drains, stents, meshes, cardiac valves, dressings, pins, clamps, clips, tubings, controlled drug delivery systems, and the like; finishing of textiles and fibers; and consumer articles such as touch screens in personal electronic devices, computers, and automatic teller machines. Such articles of manufacture may for example be metal, glass, plastic, and/or fibers.

Inventive Processes for Making the Inventive Compounds

The inventive subject matter also relates to a compound of formula I, produced by a synthetic process comprising:

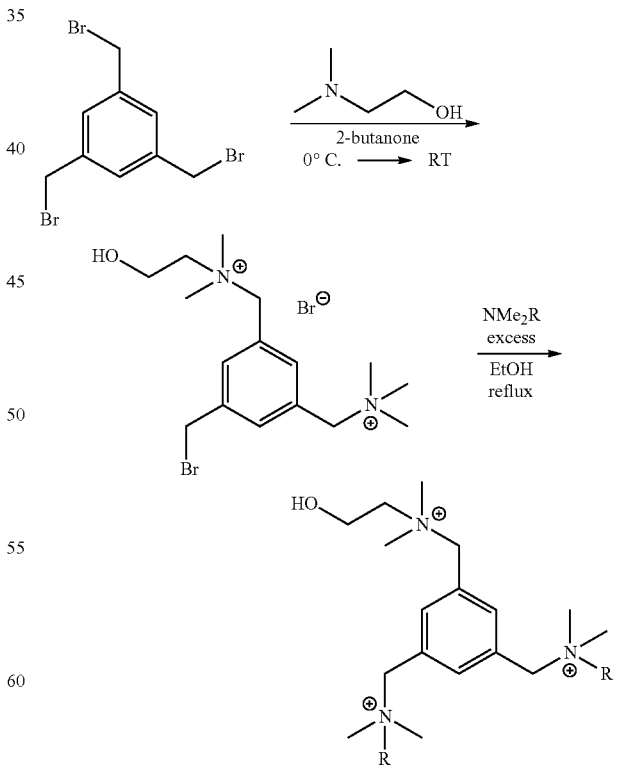

1-5 and thereafter isolating the compound of Formula I.

Inventive Pharmaceutical Compositions

The inventive subject matter also relates to a pharmaceutical composition comprising (i) an effective amount of a compound of Formula I

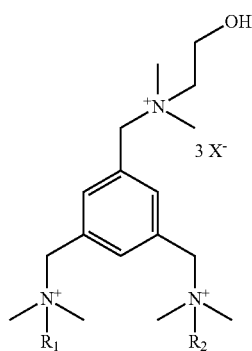

or a pharmaceutically acceptable salt, ester, or solvate thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(2-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;

m equals 1 to about 22;

n equals 1 to about 22; and (ii) a pharmaceutically acceptable carrier.

In a preferred embodiment, $R_1$ is independently selected from the group consisting of straight or branched chain $C_n$ alkyl; and $R_2$ is independently selected from the group consisting of straight or branched chain $C_m$ alkyl.

In a more preferred embodiment, $R_1$ is independently selected from the group consisting of straight chain $C_{2-18}$ alkyl; and $R_2$ is independently selected from the group consisting of straight chain $C_{2-18}$ alkyl.

In a more preferred embodiment, $R_1$ is independently selected from the group consisting of straight chain $C_{8-16}$ alkyl; and $R_2$ is independently selected from the group consisting of straight chain $C_{8-16}$ alkyl.

In a more preferred embodiment, $R_1$ is independently selected from the group consisting of straight chain $C_{10-14}$ alkyl; and $R_2$ is independently selected from the group consisting of straight chain $C_{10-14}$ alkyl.

In a more preferred embodiment, $R_1$ is $C_{12}$ alkyl; and $R_2$ is $C_{12}$ alkyl.

In another preferred embodiment, X is halogen.

In more preferred embodiment, X is bromine.

The compounds of Formulas I are 3+ cations, and as discussed above are preferably balanced by any combination of anion(s) having a total charge of 3−. Anions suitable for pharmaceutical applications are known to those of skill in the art.

The novel pharmaceutical compositions of the inventive subject matter include a therapeutically effective amount of the active agent indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the inventive subject matter.

The compounds of the inventive subject matter are preferably delivered to the patient by means of a pharmaceutically acceptable carrier. Such carriers are well known in the art and generally will be in either solid or liquid form. Solid form pharmaceutical preparations which may be prepared according to the inventive subject matter include powders, tablets, dispersible granules, capsules, cachets and suppositories. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As another example, these may be water or water/propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid pharmaceutical preparations may comprise up to 100% by weight of the subject active agent.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the inventive subject matter may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that compounds of the inventive subject matter will display significant adverse interactions with other synthetic or naturally occurring substances. Thus, an inventive compound or composition optionally is administered in combination with other antimicrobial compounds and compositions. In particular the inventive compounds and compositions are optionally administered or otherwise used in combination with other inventive compounds and compositions, or other antimicrobial substances. For example, an inventive compound or composition may be administered in combination with any one the large number of antibiotics known in the art.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the present therapeutic agents of the inventive subject matter.

Inventive Methods of Treating Infection

The inventive subject matter further relates to administering an effective amount of a compound or pharmaceutical composition comprising a compound of Formula I, to a subject in need thereof:

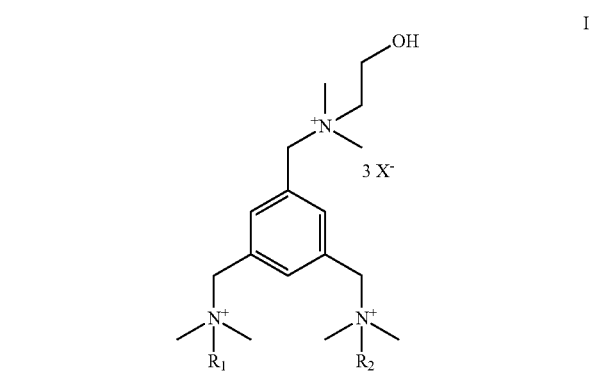

or a pharmaceutically acceptable salt, ester, or solvate thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(2-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CO_2^{(-)}$, other alkyl carboxylates, polyanions, and combinations thereof;

m equals 1 to about 22;

n equals 1 to about 22; and (ii) a pharmaceutically acceptable carrier.

In a preferred embodiment, $R_1$ is independently selected from the group consisting of straight or branched chain $C_n$ alkyl; and $R_2$ is independently selected from the group consisting of straight or branched chain $C_m$ alkyl.

In a more preferred embodiment, $R_1$ is independently selected from the group consisting of straight chain $C_{2-18}$ alkyl; and $R_2$ is independently selected from the group consisting of straight chain $C_{2-18}$ alkyl.

In a more preferred embodiment, $R_1$ is independently selected from the group consisting of straight chain $C_{8-16}$ alkyl; and $R_2$ is independently selected from the group consisting of straight chain $C_{8-16}$ alkyl.

In a more preferred embodiment, $R_1$ is independently selected from the group consisting of straight chain $C_{10-14}$ alkyl; and $R_2$ is independently selected from the group consisting of straight chain $C_{10-14}$ alkyl.

In a more preferred embodiment, $R_1$ is $C_{12}$ alkyl; and $R_2$ is $C_{12}$ alkyl.

In another preferred embodiment, X is halogen.

In more preferred embodiment, X is bromine.

Therapeutic Route(s) of Administration

Therapeutic route(s) of administration of the compounds and compositions of the inventive subject matter are well known to those skilled in the art (see, for example, "Remington's Pharmaceutical Sciences", 18th Edition, Chapter 86, pp. 1581-1592, Mack Publishing Company, 1990). The compounds and compositions may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intramuscular, intraperitoneally, intrathecally, intraventricularly, intrasternal, and intracranial injection or infusion techniques.

The compounds and compositions may be administered in the form of sterile injectable preparations, for example, as sterile injectable aqueous or oleaginous suspensions. These suspensions, may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, the compounds and compositions may be administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. An oral dosage form may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

Furthermore, the compounds may be administered topically, especially when the conditions addressed for treatment involve areas or organs readily accessible by topical application, including the lower intestinal tract. Suitable topical formulations can be readily prepared for such areas or organs. For example, topical application to the lower intestinal tract can be effected in a rectal suppository formulations (see above) or in suitable enema formulations. Other topical formulations for other purposes and body locations may be prepared according to methods of formulation known to those of skill in the art.

It is envisioned that the continuous administration or sustained delivery of the compounds and compositions of the inventive subject matter may be advantageous for a given condition. While continuous administration may be accomplished via a mechanical means, such as with an infusion pump, it is contemplated that other modes of continuous or near continuous administration may be practiced. For example, such administration may be by subcutaneous or muscular injections as well as oral pills.

Techniques for formulating a variety of other sustained- or controlled-delivery means, such as liposome carriers, bio-erodible particles or beads and depot injections, are also known to those skilled in the art.

EXAMPLES

The following examples are illustrative of the inventive subject matter and are not intended to be limitations thereon. Unless otherwise indicated, all percentages are based upon 100% by weight of the final composition.

Example 1

Synthesis of Triscationic Amphiphiles

The following example illustrates the preparation of preferred active agents provided according to the inventive subject matter. Compound numbers corresponding to the Schemes and Tables herein are indicated in bold. The inventive compounds are readily prepared by standard techniques of organic chemistry, utilizing the general synthetic pathways and procedures depicted below.

Each of the amphiphiles in this application was prepared in two steps, as shown in Scheme 1.

Scheme 1. Synthesis of amphiphiles in the M-E series.

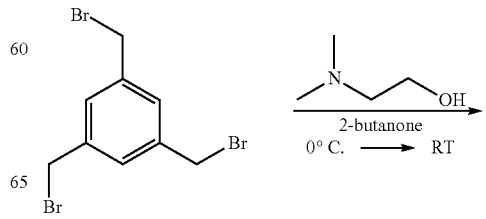

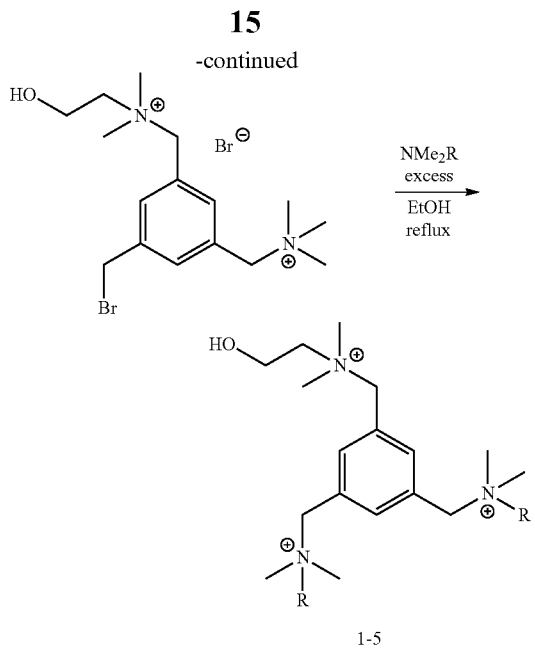

Scheme 1. Synthesis of Amphiphiles in the M-E Series

In the preparation of the compounds of the inventive subject matter, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the inventive subject matter.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

Example 2

Critical Aggregation Concentration and Degree of Ionization

Isothermal titration calorimetry (ITC) was used to determine the critical aggregation concentration (CAC) and the degree of ionization at 37° C. associated with aggregate formation for each amphiphile for the M-E series, as shown in Table 1.

TABLE 1

Table 1. Critical micelle concentration and degree of ionization at 37° C. for the M-E series.

| Compound | Tail Length (n for M-E,n,n) | CAC [mM] | Degree of Ionization |
|---|---|---|---|
| 2 | 10,10 | 9.5 | 0.24 |
| 3 | 12,12 | 1.9 | 0.20 |
| 4 | 14,14 | 0.47 | 0.18 |
| 5 | 16,16 | 0.12 | 0.15 |

A Nano ITC was used to measure the heat change associated with the deaggregation of amphiphiles via power compensation. A concentrated aqueous solution of amphiphile (>>CAC) was titrated into a thermally controlled sample cell, initially containing pure water, in a series of discrete injections. Isothermal titration calorimetry was used to determine the critical aggregation concentration (CAC).

As shown in Table 1, the compounds exhibit a decrease in CAC as tail length increases. CAC values for the M-E series are approximately equivalent for each tail length, following a linear plot of log(CAC) versus tail length, according to the equation:

$$\log(CAC) = A - Bn \quad (1)$$

where A and B are constants and n is the number of carbons in each hydrocarbon tail. The dependence of CAC on tail length is the same for each series (B=0.31).

Example 3

Minimum Inhibitory Concentration

Experiment 1. The MIC values of compounds from the M-E series were determined for one Gram-positive (*Staphylococcus aureus*) and four Gram-negative (*Escherichia coli* and *Pseudomonas aeruginosa*) strains are shown in Table 2.

TABLE 2

Minimum inhibitory concentration (MIC, µM) for compounds 3-5.

| Compound | M-E series | Pa1 (G⁻) | Pa2 (G⁻) | *P. aeruginosa* (G⁻) | *E. coli* (G⁻) | *S. aureus* (G⁺) |
|---|---|---|---|---|---|---|
| 3 | M-E, 12, 12 | 8 | 8 | 8 | 4 | 4 |
| 4 | M-E, 14, 14 | 250 | 250 | 125 | 8 | 8 |
| 5 | M-E, 16, 16 | >250 | >250 | 125 | 63 | 63 |

The derivative with two 12-carbon chains, compound 3 (M-E,12,12) has the lowest MIC values against each strain with a value of 4 µM for Gram-positive bacteria and 4-8 µM for Gram-negative bacteria. This trend is indicative of the relationship between solubility and bioactivity. Higher MIC values against Gram-negative strains may be due to their outer membrane, which is not present in Gram-positive bacteria.

Many antibacterial agents are ineffective against *P. aeruginosa* due to its semipermeable outer membrane and production of efflux pumps and β-lactamases. The contamination of medical equipment with *P. aeruginosa* biofilms contributes to hospital-acquired infections, particularly caused by antibiotic-resistant strains. While other antibacterial agents fail to inhibit *P. aeruginosa*, the amphiphiles tested, compound 3 (M-E,12,12), kills this organism at relatively low concentrations, which would be expected to be highly useful in a healthcare setting. Notably, the MIC value of compound 3 (M-E,12,12) against *P. aeruginosa*, 8 µM, is comparable to those of tobramycin at 6.4 µM, which is commonly used to treat infection in cystic fibrosis patients, and cefepime at 12.5 µM, an antispeduomonal cephalosporin.

MIC values were generally significantly below CAC values, demonstrating that amphiphile aggregation is not required to kill bacteria. At concentrations near or above the CAC, the amphiphile may act as a detergent, solubilizing the cell membrane—a mechanism of action that could be detrimental to prokaryotic cells Amphiphiles at sub-CAC levels are potent antibacterials at concentrations where detergent effects are not observed. It is recognized that CAC values reported here, measured in pure water, may differ to some degree from the CAC values in the medium used for MIC studies.

Experiment 2. The MIC values of compounds from the M-E series were determined for two Gram-negative (*Escherichia coli* and *Pseudomonas aeruginosa*) strains and five Gram-positive (*E. faecalis, S. aureus, B. subtilis, S. agalactiae,* and *B. anthracis*) strains are shown in Table 3.

2. Working stock: Overnight liquid culture diluted down to a bacterial concentration of approximately 5×10^6 CFU/mL in fresh LB
3. Plate inoculation: Sterile 96-well microtiter plate inoculated with working stock: Row A (12 wells): 100 µL sterile LB (blank) and Rows B-H (84 wells): 100 µL *P. aeruginosa* working stock; Plate covered with plastic cover, parafilm wrapped around edges; Incubate 24 hours at 37 degrees C. (stationary incubator) to establish biofilm
4. Treatment: Row A and B: 100 µL sterile PBS (blank and negative control for disruption, respectively); Rows C-H: 100 µL compound being tested, 500-4 µM concentrations (½ dilutions) in triplicate for each concentration; Plate covered, wrapped with fresh parafilm, incubated at 37 degrees C. for 24 hours
5. Staining and quantification: Plate rinsed twice with 1×PBS and allowed to dry; Wells stained with 100 µL 0.1% Crystal Violet dye for 15 minutes, excess rinsed off with gentle running dI water, allowed to dry; Stain dissolved in 100 µL 95% ethanol per well for 1 hour; Ethanol/CV solution transferred to fresh 96-well plate; Plate read at 570 nm on spectrophotometer plate reader; Values for rows C-H compared to row B (neg. control for disruption) to obtain % biofilm disruption at each concentration.

Figure 3:
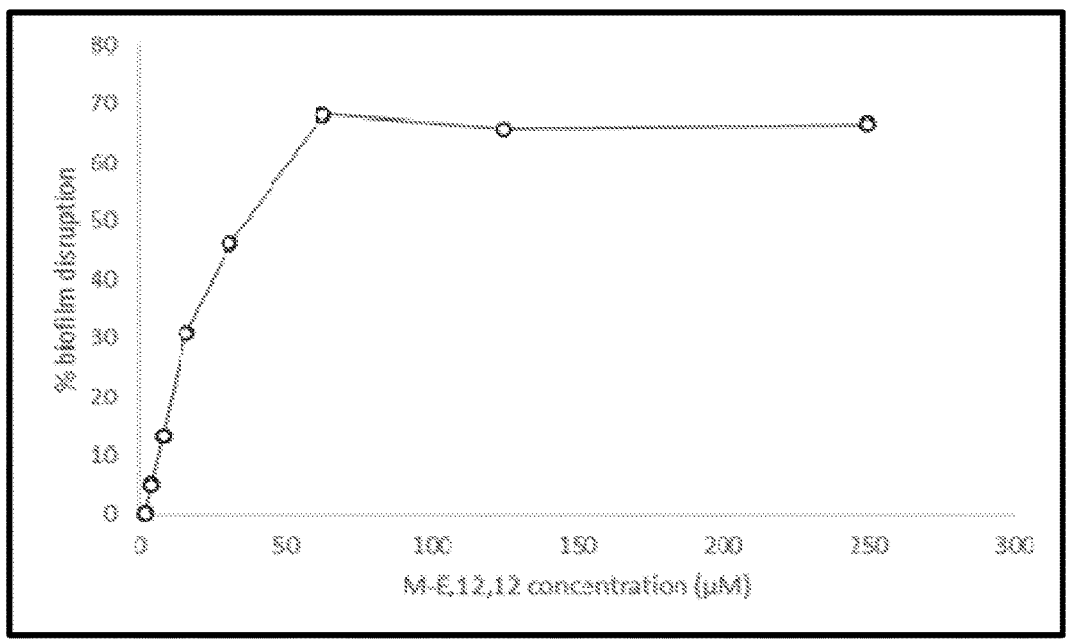
FIG. 3 is a comparative graph which depicts percent *Pseudomonas aeruginosa* biofilm disruption for exemplary inventive compound, M-E, 12,12.
Figure 4:
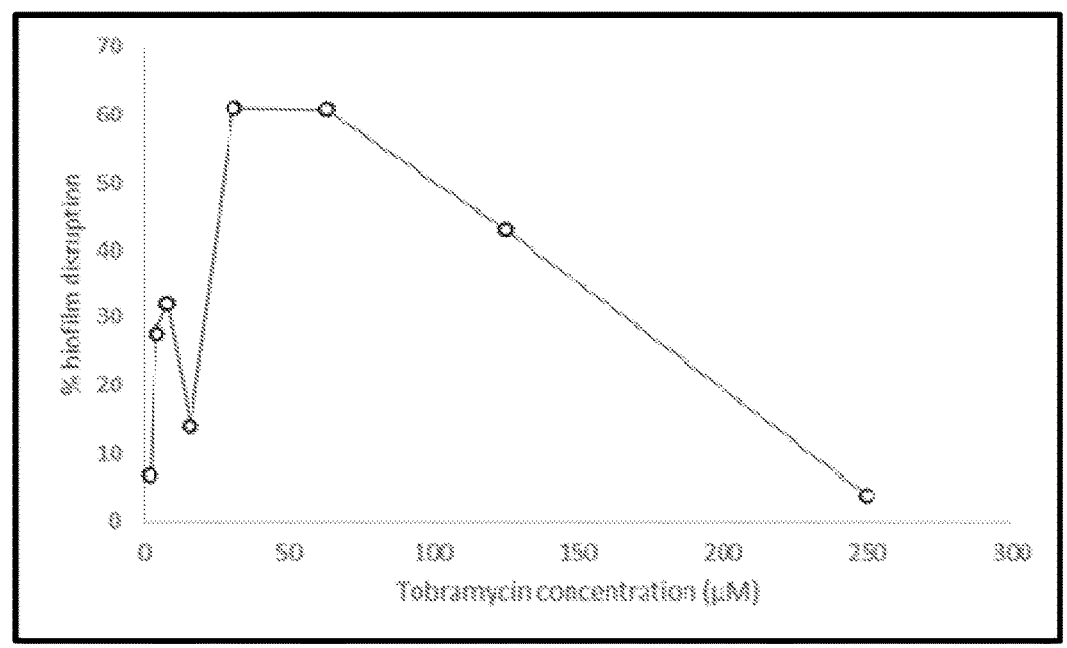
FIG. 4 is a comparative graph which depicts percent *Pseudomonas aeruginosa* biofilm disruption for tobramycin.

The described Crystal Violet Biofilm Disruption Assay was used to determine the percent biofilm disruption for the M-E 12,12 compound as shown in Table 4 and, for comparison, Tobramycin, as shown in Table 5. These results are depicted graphically in FIG. 3 and FIG. 4. Applicants have found that disruption of 50% of the biofilm by the M-E 12,12

TABLE 3

Minimum inhibitory concentration (MIC, µM) for ME-series compounds

| Compound ME, n, n | *P. aeruginosa* (G−) | *E. coli* (G−) | *E. faecalis* (G+) | *S. aureus* (G+) | *B. subtilis* (G+) | *S. agalactiae* (G+) | *B. anthracis* (G+) |
| --- | --- | --- | --- | --- | --- | --- | --- |
| 8, 8 | >250 | >250 | 63 | 250 | 250 | 125 | 63 |
| 10, 10 | 250 | 125 | 4 | 125 | 16 | 4 | 4 |
| 12, 12 | 8 | 4 | 2 | 4 | 4 | 2 | 2 |
| 14, 14 | 125 | 8 | 4 | 8 | 8 | 4 | 8 |
| 16, 16 | 125 | 63 | 63 | 63 | >250 | >250 | >250 |

As was the case for the bacterial species tested in Experiment 1 above, compound 3 (M-E,12, 12) has the lowest MIC values against each strain tested in Experiment 2.

Example 4

Biofilm Disruption Assay

A Crystal Violet Biofilm Disruption Assay was adapted from the techniques described in Bendouah, et al. 2006, *Biofilm formation by Staphylococcus aureus and Pseudomonas aeruginosa is associated with an unfavorable evolution after surgery for chronic sinusitis and nasal polyposis*, Otolaryngol. Head and Neck Surg. 134:991-6. doi: 10.101/j.otohns.2006.03.001 and Hochbaum, et al. 2011, *Inhibitory effects of D-amino acids on Staphylococcus aureus biofilm development*, J. Bacteriol. 193 (20):5616-22. doi: 10.1128/JB.05534-11, which are incorporated by reference in their entirety. Applicants' adapted assay was performed as follows:

1. Bacterial growth: *Pseudomonas aeruginosa* grown in 1× Luria broth (LB) at 37 degrees C. (120 RPM in shaking incubator) for 24 hours compound is within a single dilution of tobramycin, which is a standard treatment for some difficult *Pseudomonas* infections. This data in conjunction with the low MIC for this compound demonstrates the promise of the inventive compounds.

TABLE 4

Table 4. % biofilm disruption for compound M-E,12,12

| M-E,12,12 | % disruption | | |
| --- | --- | --- | --- |
| Conc. (µM) | trial 1 | trial 2 | average |
| 250 | 67.34359069 | 65.60913257 | 66.47636 |
| 125 | 65.03599345 | 66.28771368 | 65.66185 |
| 63 | 72.05394383 | 64.21898378 | 68.13646 |
| 31 | 61.1005036 | 30.92609828 | 46.0133 |
| 16 | 47.344981 | 14.23017565 | 30.78758 |
| 8 | 24.05999938 | 2.816818444 | 13.43841 |
| 4 | 1.758890228 | 8.48108573 | 5.119988 |
| 2 | 0 | 0 | 0 |

Max % disruption 68%
Min conc. >50% disruption 63 µM

TABLE 5

Table 5. % biofilm disruption for Tobramycin

| Tobramycin Conc. (μM) | % disruption | | |
|---|---|---|---|
| | trial 1 | trial 2 | average |
| 250 | 0 | 7.606598 | 3.803299 |
| 125 | 34.87889 | 51.26219 | 43.07054 |
| 63 | 53.5149 | 68.06567 | 60.79029 |
| 31 | 51.89102 | 70.12858 | 61.0098 |
| 16 | 0 | 27.9612 | 13.9806 |
| 8 | 15.46407 | 48.78756 | 32.12581 |
| 4 | 0 | 55.3151 | 27.65755 |
| 2 | 0 | 13.61519 | 6.807596 |
| Max % disruption | 61% | | |
| Min conc. >50% disruption | 31 μM* | | |

*decrease in disruption at higher concentrations (>63 μM)

Example 5

General Laboratory Methods

Synthesis and Analysis

All solvents and reagents were used as received from the indicated chemical supplier unless otherwise specified. Melting points for solids were measured using a Mel-Temp apparatus with a digital thermometer (uncorrected). Nuclear magnetic resonance spectra were collected using one of the following instruments, as noted: Bruker-Spectrospin 400 ('H: 400 MHz, $^{13}$C: 100 MHz) or Bruker-Spectrospin 300 ('H: 300 MHz, $^{13}$C: 75 MHz). NMR Spectra were analyzed using Bruker TopSpin software, version 3.2. The solvent residual peak was used as a reference. $^{13}$C NMR peaks are reported to one place, unless signals differ by <0.15 ppm, in which case peaks are reported to two places. Exact mass measurements were obtained in flow injection experiments on a 6224 time of flight mass spectrometer (TOF-MS) (Agilent Technologies, Santa Clara, Calif.). Compounds were ionized by positive ion electrospray (ESI) under the following conditions: capillary voltage, +2500V, nozzle voltage, 500 V; fragmentor voltage, 175 V; drying gas temperature, 325° C.; drying gas flow, 5 L/min; nebulizer, 40 psi. MS data was collected in full scan mode (500 ms/scan) over the range of 100-1700 m/z. Mass errors were less than 5 ppm for all observed compounds. Mass resolving power, m/Δm, was ~19,000 at 922 m/z. Mass Hunter software version B.04 was used for all data acquisition and analysis.

Isothermal Titration Calorimetry

CAC and $\Delta H_{agg}$ were determined using a Nano-ITC (TA-Instruments). Prior to each experiment the sample cell was washed with $dH_2O$ (300 mL), ethanol (100 mL), $dH_2O$ (300 mL) and nanopure water (200 mL). Next, 950 μL of nanopure water was added to the sample cell. A concentrated aqueous solution (>>CAC) of amphiphile was prepared and equilibrated at 37° C. A 250 μL syringe was filled with the aqueous solution, and loaded into the Nano ITC. Multiple single injections in aliquots of 5 μL were injected into the sample cell with time intervals varying from 300 s to 1400 s. Samples were continuously stirred (300 rpm) throughout the titration. The Nano-Analyze program (TA-Instruments) was used to analyze the data. CAC and $\Delta H_{agg}$ values reported are the average of two or more repeat experiments for each amphiphile.

Bacterial Strains and Growth Conditions

The Gram-positive bacterial strains used tested were *Staphylococcus aureus* subsp. *aureus* ATCC® 29213™, *Enterococcus faecalis* ATCC® 29212™, *Bacillus cereus*, and *Streptococcus agalactiae* J48.[58] The Gram-negative bacterial strains used were *Escherichia coli* ATCC® 25922™ and *Pseudomonas aeruginosa* ATCC® 27853™. All strains were grown in 1× Mueller-Hinton Broth at 37° C. for 12-24 h. For the MIC and combination studies, bacterial suspensions were prepared by diluting overnight cultures to 5×10⁶ CFU/mL in 2× Mueller-Hinton Broth, so that when amphiphile solutions are added the final broth strength is 1×.

Minimum Inhibitory Concentration and Minimum Bactericidal Concentration

The methods used to determine the MIC and MBC were performed as previously described and followed the standards set forth by the Clinical and Laboratory Standards Institute (See Ladow, J. E.; Warnock, D. C.; Hamill, K. M.; Simmons, K. L.; Davis, R. W.; Schwantes, C. R.; Flaherty, D. C.; Willcox, J. A. L.; Wilson-Henjum, K.; Caran, K. L.; Minbiole, K. P. C.; Seifert, K. Bicephalic amphiphile architecture affects antibacterial activity. *Eur. J. Med. Chem.* 2011, 46, 4219-4226 and P. A. Wayne Methods for dilution antimicrobial tests for bacteria that grow aerobically. 2009.). Briefly, compounds were serially diluted and 100 μL of each dilution were added to the wells of a 96-well flat-bottomed microtiter plate in triplicate. After adding 100 μL of the bacterial cell suspension, the plates were incubated at 37° C. for 72 h. The MIC of the compound was defined as the minimum concentration that resulted in visible inhibition of bacterial growth. In order to determine the MBC, a 100 μl aliquot from each triplicate well was grown on Todd-Hewitt agar and incubated for 24 h at 37° C. The MBC was defined as the concentration of the compound that resulted in a 99.9% reduction of the bacterial CFU/mL. The MIC was considered to be bactericidal if the MBC was the same concentration or one concentration higher in the dilution series as the MIC, per Motyl, M.; Dorso, K.; Barrett, J.; Giacobbe, R. Basic microbiological techniques used in antibacterial drug discovery. *Curr. Protoc. Pharmacol.* 2006, Chapter 13.

Combination Studies

To determine if two amphiphiles act synergistically to kill *E. coli* or *S. aureus*, combination studies were performed using the checkerboard technique as described in Giacometti, A.; Cirioni, O.; Del Prete, M. S.; Paggi, A. M.; D'Errico, M. M.; Scalise, G. Combination studies between polycationic peptides and clinically used antibiotics against Gram-positive and Gram-negative bacteria. *Peptides.* 2000, 21, 1155-1160 Amphiphiles with MIC values higher than the maximum concentration used (>250 μM) were excluded from the combination studies. The amphiphile concentrations used in the combination studies ranged from ¹⁄₁₆ to 2× the MIC. Fifty microliters of each amphiphile dilution and 100 μL of the bacterial suspension were added to the wells of a 96-well flat-bottomed microtiter plate. Control wells consisted of the bacterial suspension treated with media alone and bacteria treated with individual amphiphiles. Plates were incubated at 37° C. for 72 h. The FIC index was calculated using the following formula: $FIC = FIC_A + FIC_B = A/MIC_A + B/MIC_B$. A and B are the MIC values of compound A and compound B when combined, and $MIC_A$ and $MIC_B$ are the MIC of compound A and B alone. A combination was considered to be synergistic if the FIC was less than 0.5; a combination was considered indifferent with an FIC of 0.5-4; and a combination was considered antagonistic with an FIC>4. The FIC indices of synergistic combinations were confirmed in two separate experiments.

REFERENCES

The following literature references are believed to useful to an understanding of the inventive subject matter in the context of its place in the relevant art. Citation here is not to be construed as an assertion or admission that any reference cited is material to patentability of the inventive subject matter. Applicants will properly disclose information material to patentability in an Information Disclosure Statement. Each of the following documents is hereby incorporated by reference in its entirety in this application:

1. Fan, F. F. Defining and Combating the Mechanisms of Triclosan Resistance in Clinical Isolates of *Staphylococcus aureus. Antimicrob. Agents Chemother.* 2002, 46, 3343-3347.
2. Chea, P. Executive summary: Select findings, conclusions, and policy recommendations. *Clinical Infectious Diseases.* 2005, 41, S224-S227.
3. Gilbert, M.; MacDonald, J.; Louie, M.; Gregson, D.; Zhang, K.; Elsayed, S.; Laupland, K.; Nielsen, D.; Wheeler, V.; Lye, T.; Conly, J. Prevalence of USA300 colonization or infection and associated variables during an outbreak of community-associated methicillin-resistant *Staphylococcus aureus* in a marginalized urban population. *Canadian Journal of Infectious Diseases and Medical Microbiology.* 2007, 18, 357-362.
4. Okeke, I. N.; Lamikanra, A.; Edelman, R. Socioeconomic and behavioral factors leading to acquired bacterial resistance to antibiotics in developing countries. *Emerging Infectious Diseases.* 1999, 5, 18-27.
5. Taubes, G. The bacteria fight back. *Science.* 2008, 321, 356-360+361.
6. Scheffler, R. J.; Colmer, S.; Tynan, H.; Demain, A. L.; Gullo, V. P. Antimicrobials, drug discovery, and genome mining *Appl. Microbiol. Biotechnol.* 2013, 97, 969-978.
7. Anonymous. Evolving threat of antimicrobial resistance. *WHO DRUG INF.* 2012, 26, 125-125.
8. Anonymous. Antibiotic Resistance Threats in the United States, 2013. *Medical Benefits.* 2014, 31, 12-12.
9. Johnston, B. L.; Bryce, E. Hospital infection control strategies for vancomycin-resistant *Enterococcus*, methicillin-resistant *Staphylococcus aureus* and *Clostridium difficile. Can. Med. Assoc. J.* 2009, 180, 627-631.
10. Goldmann, D. A.; Weinstein, R. A.; Wenzel, R. P.; Tablan, O. C.; Duma, R. J.; Gaynes, R. P.; Schlosser, J.; Martone, W. J. Strategies to prevent and control the emergence and spread of antimicrobial-resistant microorganisms in hospitals: A challenge to hospital leadership. *J. Am. Med. Assoc.* 1996, 275, 234-240.
11. Kumar Gautam, C.; Kumar Srivastav, A.; Bind, S.; Madhav, M.; Shanthi, V. An insight into biofilm ecology and its applied aspects. *International Journal of Pharmacy and Pharmaceutical Sciences.* 2013, 5, 69-73.
12. Larson, E. L.; Early, E.; Cloonan, P.; Sugrue, S.; Parides, M. An organizational climate intervention associated with increased handwashing and decreased nosocomial infections. *Behavioral Medicine.* 2000, 26, 14-22.
13. MacDonald, A.; Dinah, F.; MacKenzie, D.; Wilson, A. Performance feedback of hand hygiene, using alcohol gel as the skin decontaminant, reduces the number of inpatients newly affected by MRSA and antibiotic costs. *J. Hosp. Infect.* 2004, 56, 56-63.
14. Gerhard Domagk A new class of disinfectants. *Dtsch med Wochenschr.* 1935, 61, 829-832.
15. Ladow, J. E.; Warnock, D. C.; Hamill, K. M.; Simmons, K. L.; Davis, R. W.; Schwantes, C. R.; Flaherty, D. C.; Willcox, J. A. L.; Wilson-Henjum, K.; Caran, K. L.; Minbiole, K. P. C.; Seifert, K. Bicephalic amphiphile architecture affects antibacterial activity. *Eur. J. Med. Chem.* 2011, 46, 4219-4226.
16. Grenier, M. C.; Davis, R. W.; Wilson-Henjum, K. L.; LaDow, J. E.; Black, J. W.; Caran, K. L.; Seifert, K.; Minbiole, K. P. C. The antibacterial activity of 4,4'-bipyridinium amphiphiles with conventional, bicephalic and gemini architectures. *Bioorg. Med. Chem. Lett.* 2012, 22, 4055-4058.
17. Maisuria, B. B.; Actis, M. L.; Hardrict, S. N.; Falkinham III, J. O.; Cole, M. F.; Cihlar, R. L.; Peters, S. M.; Macri, R. V.; Sugandhi, E. W.; Williams, A. A.; Poppe, M. A.; Esker, A. R.; Gandour, R. D. Comparing micellar, hemolytic, and antibacterial properties of di- and tricarboxyl dendritic amphiphiles. *Bioorg. Med. Chem.* 2011, 19, 2918-2926.
18. Macri, R. V.; Karlovská, J.; Doncel, G. F.; Du, X.; Maisuria, B. B.; Williams, A. A.; Sugandhi, E. W.; Falkinham III, J. O.; Esker, A. R.; Gandour, R. D. Comparing anti-HIV, antibacterial, antifungal, micellar, and cytotoxic properties of tricarboxylato dendritic amphiphiles. *Bioorg. Med. Chem.* 2009, 17, 3162-3168.
19. Sugandhi, E. W.; Falkinham III, J. O.; Gandour, R. D. Synthesis and antimicrobial activity of symmetrical two-tailed dendritic tricarboxylato amphiphiles. *Bioorg. Med. Chem.* 2007, 15, 3842-3853.
20. Sugandhi, E. W.; Macri, R. V.; Williams, A. A.; Kite, B. L.; Slebodnick, C.; Falkinham, J. O.; Esker, A. R.; Gandour, R. D. Synthesis, Critical Micelle Concentrations, and Antimycobacterial Properties of Homologous, Dendritic Amphiphiles. Probing Intrinsic Activity and the "Cutoff" Effect. *J. Med. Chem.* 2007, 50, 1645-1650.
21. Williams, A. A.; Sugandhi, E. W.; Macri, R. V.; Falkinham, J. O.; Gandour, R. D. Antimicrobial activity of long-chain, water-soluble, dendritic tricarboxylato amphiphiles. *Journal of Antimicrobial Chemotherapy.* 2007, 59, 451-458.
22. Falkinham III, J. O.; Macri, R. V.; Maisuria, B. B.; Actis, M. L.; Sugandhi, E. W.; Williams, A. A.; Snyder, A. V.; Jackson, F. R.; Poppe, M. A.; Chen, L.; Ganesh, K.; Gandour, R. D. Antibacterial activities of dendritic amphiphiles against nontuberculous mycobacteria. *Tuberculosis.* 2012, 92, 173-181.
23. Ator, L. E.; Jennings, M. C.; McGettigan, A. R.; Paul, J. J.; Wuest, W. M.; Minbiole, K. P. C. Beyond paraquats: dialkyl 3,3'- and 3,4'-bipyridinium amphiphiles as antibacterial agents. *Bioorg. Med. Chem. Lett.* 2014, 24, 3706-3709.
24. Black, J. W.; Jennings, M. C.; Azarewicz, J.; Paniak, T. J.; Grenier, M. C.; Wuest, W. M.; Minbiole, K. P. C. TMEDA-derived biscationic amphiphiles: An economical preparation of potent antibacterial agents. *Bioorg. Med. Chem. Lett.* 2014, 24, 99-102.
25. Scamehorn, J. F.; Sabatini, D. A.; Harwell, J. H. Surfactants, Part I: Fundamentals. In *Encyclopedia of Supramolecular Chemistry* Marcel Dekker: New York, 2004; pp 1458.
26. Pohorille, A.; Deamer, D. Self-assembly and function of primitive cell membranes. *Res. Microbiol.* 2009, 160, 449-456.
27. Soontravanich, S.; Munoz, J. A.; Scamehorn, J. F.; Harwell, J. H.; Sabatini, D. A. Interaction between an anionic and an amphoteric surfactant. Part I: Monomer-micelle equilibrium. *Journal of Surfactants and Detergents.* 2008, 11, 251-261.
28. Haldar, J.; Kondaiah, P.; Bhattacharya, S. Synthesis and antibacterial properties of novel hydrolyzable cationic amphiphiles. Incorporation of multiple head groups leads to impressive antibacterial activity. *J. Med. Chem.* 2005, 48, 3823-3831.

29. Geraldo, I. M.; Gilman, A.; Shintre, M. S.; Modak, S. M. Rapid antibacterial activity of 2 novel hand soaps: evaluation of the risk of development of bacterial resistance to the antibacterial agents. *Infect. Control Hosp. Epidemiol.* 2008, 29, 736-741.

30. Hiraki, Y.; Yoshida, M.; Masuda, Y.; Inoue, D.; Tsuji, Y.; Kamimura, H.; Karube, Y.; Takaki, K.; Kawano, F. Successful treatment of skin and soft tissue infection due to carbapenem-resistant *Acinetobacter baumannii* by ampicillin-sulbactam and meropenem combination therapy. *International Journal of Infectious Diseases.* 2013, 17, e1234-e1236.

31. Sick, A. C.; Tschudin-Sutter, S.; Turnbull, A. E.; Weissman, S. J.; Tamma, P. D. Empiric Combination Therapy for Gram-Negative Bacteremia. *Pediatrics.* 2014.

32. Daikos, G. L.; Petrikkos, P.; Psichogiou, M.; Kosmidis, C.; Vryonis, E.; Skoutelis, A.; Georgousi, K.; Tzouvelekis, L. S.; Tassios, P. T.; Bamia, C.; Petrikkos, G. Prospective observational study of the impact of VIM-1 metallo-beta-lactamase on the outcome of patients with *Klebsiella pneumoniae* bloodstream infections. *Antimicrob. Agents Chemother.* 2009, 53, 1868-1873.

33. Drew, K. R. P.; Sanders, L. K.; Culumber, Z. W.; Zribi, O.; Wong, G. C. L. Cationic Amphiphiles Increase Activity of Aminoglycoside Antibiotic Tobramycin in the Presence of Airway Polyelectrolytes. *J. Am. Chem. Soc.* 2009, 131, 486-493.

34. Sattar, S., A.; Springthorpe, V., S.; Karim, Y.; Loro, P. Chemical disinfection of non-porous inanimate surfaces experimentally contaminated with four human pathogenic viruses. *Epidemiol. Infect.* 1989, 102, 493-505.

35. Harrison, J. J.; Turner, R. J.; Joo, D. A.; Stan, M. A.; Chan, C. S.; Allan, N. D.; Vrionis, H. A.; Olson, M. E.; Ceri, H. Copper and quaternary ammonium cations exert synergistic bactericidal and antibiofilm activity against *Pseudomonas aeruginosa*. *Antimicrob. Agents Chemother.* 2008, 52, 2870-2881.

36. Shintre, M. S.; Gaonkar, T. A.; Modak, S. M. Efficacy of an alcohol-based healthcare hand rub containing synergistic combination of farnesol and benzethonium chloride. *Int. J. Hyg. Environ. Health.* 2006, 209, 477-487.

37. Dymond, M. K.; Attard, G. S. Cationic type i amphiphiles as modulators of membrane curvature elastic stress in vivo. *Langmuir.* 2008, 24, 11743-11751.

38. Wiseman, T.; Williston, S.; Brandts, J. F.; Lin, L. -. Rapid measurement of binding constants and heats of binding using a new titration calorimeter. *Anal. Biochem.* 1989, 179, 131-137.

39. Kresheck, G. C.; Hargraves, W. A. Thermometric titration studies of the effect of head group, chain length, solvent, and temperature on the thermodynamics of Micelle formation. *J. Colloid Interface Sci.* 1974, 48, 481-493.

40. Paula, S.; Süs, W.; Tuchtenhagen, J.; Blume, A. Thermodynamics of micelle formation as a function of temperature: A high sensitivity titration calorimetry study. *J. Phys. Chem.* 1995, 99, 11742-11751.

41. Heerklotz, H.; Seelig, J. Titration calorimetry of surfactant-membrane partitioning and membrane solubilization. *Biochimica et Biophysica Acta—Biomembranes.* 2000, 1508, 69-85.

42. Meyer, R. D.; Young, L. S.; Armstrong, D. Tobramycin (nebramycin factor 6): in vitro activity against *Pseudomonas aeruginosa*. *Appl. Microbiol.* 1971, 22, 1147-1151.

43. Bodey, G. P.; Ho, D. H.; LeBlanc, B. In vitro studies of BMY-28142, a new broad-spectrum cephalosporin. *Antimicrob. Agents Chemother.* 1985, 27, 265-269.

44. Gellatly, S. L.; Hancock, R. E. W. *Pseudomonas aeruginosa*: new insights into pathogenesis and host defenses. *Pathog Dis.* 2013, 67, 159-173.

45. Motyl, M.; Dorso, K.; Barrett, J.; Giacobbe, R. Basic microbiological techniques used in antibacterial drug discovery. *Curr Protoc Pharmacol.* 2006, Chapter 13, Unit13A.3.

46. Giacometti, A.; Cirioni, O.; Del Prete, M. S.; Paggi, A. M.; D'Errico, M. M.; Scalise, G. Combination studies between polycationic peptides and clinically used antibiotics against Gram-positive and Gram-negative bacteria. *Peptides.* 2000, 21, 1155-1160.

47. Lister, P. D.; Wolter, D. J. Levofloxacin-Imipenem Combination Prevents the Emergence of Resistance among Clinical Isolates of *Pseudomonas aeruginosa*. *Clinical Infectious Diseases.* 2005, 40, S105-S114.

48. Hiraki, Y.; Yoshida, M.; Masuda, Y.; Inoue, D.; Tsuji, Y.; Kamimura, H.; Karube, Y.; Takaki, K.; Kawano, F. Successful treatment of skin and soft tissue infection due to carbapenem-resistant *Acinetobacter baumannii* by ampicillin-sulbactam and meropenem combination therapy. *International Journal of Infectious Diseases.* 2013, 17, e1234-e1236.

49. Gribble, M. J.; Chow, A. W.; Naiman, S. C.; Smith, J. A.; Bowie, W. R.; Sacks, S. L.; Grossman, L.; Buskard, N.; Growe, G. H.; Plenderleith, L. H. Prospective randomized trial of piperacillin monotherapy versus carboxypenicillin-aminoglycoside combination regimens in the empirical treatment of serious bacterial infections. *Antimicrob. Agents Chemother.* 1983, 24, 388-393.

50. Best, M.; Kennedy, M. E.; Coates, F. Efficacy of a variety of disinfectants against *Listeria* spp. *Appl. Environ. Microbiol.* 1990, 56, 377-380.

51. Tebbs, S. E.; Elliott, T. S. A novel antimicrobial central venous catheter impregnated with benzalkonium chloride. *J. Antimicrob. Chemother.* 1993, 31, 261-271.

52. Price, P. B. Benzalkonium Chloride (Zephiran Chloride®) as a Skin Disinfectant. *Archives of Surgery.* 1950, 61, 23.

53. Seifert, K. N.; McArthur, W. P.; Bleiweis, A. S.; Brady, L. J. Characterization of group B streptococcal glyceraldehyde-3-phosphate dehydrogenase: surface localization, enzymatic activity, and protein-protein interactions. *Can. J. Microbiol.* 2003, 49, 350-356.

54. P. A. Wayne Methods for dilution antimicrobial tests for bacteria that grow aerobically. 2009.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

We claim:

1. A compound of formula I

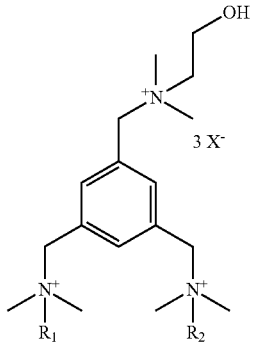

or an ester thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(2-)}$, $F^{(-)}$, $Cl^{(-)}$, $Br^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;

m equals 1 to about 22; and n equals 1 to about 22.

2. The compound of claim 1, wherein:

$R_1$ is independently selected from the group consisting of straight or branched chain $C_n$ alkyl; and $R_2$ is independently selected from the group consisting of straight or branched chain $C_m$ alkyl.

3. The compound of claim 2, wherein:

$R_1$ is independently selected from the group consisting of straight chain $C_{2-18}$ alkyl; and $R_2$ is independently selected from the group consisting of straight chain $C_{2-18}$ alkyl.

4. The compound of claim 3, wherein:

$R_1$ is independently selected from the group consisting of straight chain $C_{8-16}$ alkyl; and $R_2$ is independently selected from the group consisting of straight chain $C_{8-16}$ alkyl.

5. The compound of claim 4, wherein:

$R_1$ is independently selected from the group consisting of straight chain $C_{10-14}$ alkyl; and $R_2$ is independently selected from the group consisting of straight chain $C_{10-14}$ alkyl.

6. The compound of claim 5, wherein:

$R_1$ is $C_{12}$ alkyl; and $R_2$ is $C_{12}$ alkyl.

7. The compound of claim 1, wherein X is halogen.

8. The compound of claim 7, wherein X is bromine.

9. A method for inhibiting bacterial growth, comprising contacting a bacteria with a composition comprising (i) a compound of Formula I or (ii) a combination of two or more compounds, each independently selected from the group consisting of a compound of Formula I

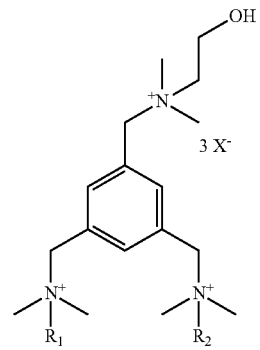

or an ester thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(2-)}$, $F^{(-)}$, $Cl^{(-)}$, $Br^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;

m equals 1 to about 22; and n equals 1 to about 22.

10. The method of claim 9, wherein:

$R_1$ is independently selected from the group consisting of straight or branched chain $C_n$ alkyl; and $R_2$ is independently selected from the group consisting of straight or branched chain $C_m$ alkyl.

11. The method of claim 10, wherein:

$R_1$ is independently selected from the group consisting of straight chain $C_{2-18}$ alkyl; and $R_2$ is independently selected from the group consisting of straight chain $C_{2-18}$ alkyl.

12. The method of claim 11, wherein:

$R_1$ is independently selected from the group consisting of straight chain $C_{8-16}$ alkyl; and $R_2$ is independently selected from the group consisting of straight chain $C_{8-16}$ alkyl.

13. The method of claim 12, wherein:

$R_1$ is independently selected from the group consisting of straight chain $C_{10-14}$ alkyl; and $R_2$ is independently selected from the group consisting of straight chain $C_{10-14}$ alkyl.

14. The method of claim 13, wherein:

$R_1$ is $C_{12}$ alkyl; and $R_2$ is $C_{12}$ alkyl.

15. The method of claim 9, wherein X is halogen.

16. The method of claim 15, wherein X is bromine.

17. The method of claim 9, wherein said composition is in a solution or other carrier in a suitable concentration for use as an environmental disinfectant.

18. The method of claim 9, wherein said composition is formulated for use as a topical personal care composition.

19. The method of claim 9, wherein said composition is formulated for use as a material coating.

20. A pharmaceutical composition comprising (i) an an amount effective to inhibit bacterial growth of a compound of Formula I

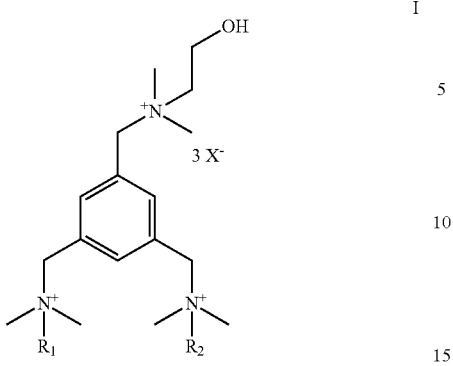

or an ester thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(2-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;

m equals 1 to about 22;

n equals 1 to about 22; and (ii) a pharmaceutically acceptable carrier.

* * * * *